United States Patent
Raymond Chia et al.

(10) Patent No.: US 6,241,726 B1
(45) Date of Patent: Jun. 5, 2001

(54) CATHETER SYSTEM HAVING A TIP SECTION WITH FIXATION MEANS

(75) Inventors: Weng-Kwen Raymond Chia, Irvine; Hosheng Tu, Tustin, both of CA (US)

(73) Assignee: Irvine Biomedical, Inc., Irvine, CA (US)

( * ) Notice: Subject to any disclaimer, the term of this patent is extended or adjusted under 35 U.S.C. 154(b) by 0 days.

(21) Appl. No.: 09/235,263

(22) Filed: Jan. 22, 1999

Related U.S. Application Data (63) Continuation-in-part of application No. 08/861,271, filed on May 21, 1997, now Pat. No. 5,891,137.

(51) Int. Cl.[7] ................................................. A61B 17/39
(52) U.S. Cl. ................................................. 606/41; 607/128
(58) Field of Search ................................... 607/122, 126, 607/128; 606/41

(56) References Cited

U.S. PATENT DOCUMENTS

| | | | |
|---|---|---|---|
| 4,841,971 | 6/1989 | Hess | 607/126 |
| 5,179,962 | 1/1993 | Dutcher et al. | 607/128 |
| 5,500,012 | 3/1996 | Brucker et al. | 607/122 |
| 5,891,137 | 4/1999 | Chia et al. | 607/128 |

*Primary Examiner*—William E. Kamm
*Assistant Examiner*—George R. Evanisko (57) ABSTRACT

A catheter system having a tip section with fixation means for use in treatment of tissues, such as mapping pulmonary veins or ablating tumors in a natural body conduit or cavity by applying RF energy, wherein the catheter system passes through a natural body opening to reach the target tissue, wherein the catheter system stays at a desired position via its fixation means having needle-like attachments, and delivers therapeutic RF energy to the target tissue for improved tissue treatment.

12 Claims, 7 Drawing Sheets

CATHETER SYSTEM HAVING A TIP SECTION WITH FIXATION MEANS

This is a continuation-in-part of application Ser. No. 08/861,271, filed May 21, 1997, now allowed by the Patent Office on May 28, 1998.

FIELD OF THE INVENTION

The present invention generally relates to novel constructions for a catheter system. More particularly, this invention relates to a mapping and/or ablation catheter system with fixation means for use in mapping and/or treatment of pulmonary veins and in other medical applications, such as ablating tumors in a natural body conduit or cavity by applying RF energy. The catheter system passes through a natural body opening to reach the target tissue, where the catheter stays in a desired position via its fixation means and maps the tissue electrical potential and/or delivers therapeutic energy to the target tissue for improved treatment.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias that are frequently caused by the presence of an "arrhythmogenic site" or "accessory atrioventricular pathway" close to the inner surface of the chambers of a heart or in pulmonary veins. The heart includes a number of normal pathways that are responsible for the propagation of electrical signals from the upper to lower chambers necessary for performing normal systole and diastole functions. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problems, usually by ablating the abnormal arrhythmogenic tissue or accessory pathway responsible for the tachycardia. It is important for a physician to accurately steer the catheter to the exact site for ablation and fix the catheter steadily at that site. Once at the site, it is important for a physician to control the emission of energy to ablate the tissue within or around the heart.

Of particular interest to the present invention are radiofrequency (RF) ablation protocols that have been proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the tip electrode to the cardiac tissue in order to ablate the tissue of arrhythmogenic site or the accessory pathway. By successfully destroying that tissue, the abnormal signal patterns responsible for the tachycardia may be eliminated.

Typically a conventional electrophysiology catheter has a tip portion that is to be inserted into a pulmonary vein for mapping and treating focal atrial fibrillations. To better monitor and control the distance of said catheter into the vein, it is preferable that a fixation means be incorporated onto the catheter shaft at a predetermined point. When the penetrating means contacts the ostium of the pulmonary vein, the catheter cannot advance any further inside the pulmonary vein and the distance of the distal portion inside the vein is determined. A major drawback for a conventional catheter without a fixation means at its distal portion is its difficulty for maintaining the tip portion in certain position; the effectiveness of mapping and ablation is significantly compromised.

The tip section of a catheter is referred to here as the portion of that catheter containing at least one electrode. For illustration purposes, a catheter utilized in the endocardial radiofrequency ablation is inserted into a major vein or artery, usually in the neck or groin area. The catheter is then guided into an appropriate chamber or pulmonary vein of the heart by appropriate manipulation through the vein or artery. The tip of a catheter must be manipulatable by a physician from the proximal end of the catheter, so that the electrodes at the tip section can be positioned against the tissue site to be mapped or ablated. The catheter must have a great deal of flexibility and steerability in order to guide the catheter to the target site of the heart. It must permit user manipulation of the tip even when the catheter body is in a curved and/or twisted configuration. The tip section of a conventional electrophysiology catheter that is deflectable usually contains one large electrode about 4 mm in length for ablation purpose.

After the exact location of a target tissue is identified, the ablation catheter may still not easily approach the target site. An external ultrasonic imaging capability therefore becomes in need so that ablation is not taking place in an inappropriate location. The fluoroscope time can be substantially cut short when an external ultrasonic imaging is used instead. In the U.S. Pat. No. 4,794,931, there has been disclosed a catheter and system which can be utilized for ultrasonic imaging. However, there is no disclosure to how such a catheter and system can be utilized in conjunction with an endocardial ablation catheter having a tip section with fixation means to achieve the desired ultrasonic imaging and ultimately the desired mapping or ablation.

While a radiofrequency electrophysiology procedure using an existing catheter has had promising results in pulmonary veins for focal atrial fibrillations, the tip section of a known catheter may not steadily stay in place for intimately contact the cardiac tissue during the mapping and/or ablation period. Therefore there is a need for an improved catheter which can be utilized for mapping and ablation and in which is possible to temporarily affix the tip section of the catheter so that it will remain in a desired position on the wall of the heart during beating of the heart.

SUMMARY OF THE INVENTION

In general, it is an object of the present invention to provide an improved catheter which can be used in mapping and/or ablating cardiac tissue in the wall of a heart and which is provided with fixation means for retaining the tip section in a desired position on the wall of the heart. In is another object of the present invention to provide a catheter system having needle-like penetrating means for securing the catheter on a tissue. The capability of affixing the tip section of the catheter in place may also be applicable to means of ablating the tumors in a body natural conduit or cavity.

In one embodiment, a catheter system comprises a catheter sheath having a distal section, a distal end, a proximal end, and at least one lumen extending between the distal end and the proximal end; a handle attached to the proximal end of said catheter sheath; an inner catheter, which is longer than said catheter sheath and is located inside the lumen of the catheter sheath, comprising a flexible elongate tubular member having a distal section, a proximal extremity and a distal extremity, at least one electrode mounted on the distal section of the flexible elongate tubular member of the inner catheter, and wherein said handle is attached to the proximal extremity of the inner catheter; the distal section of said catheter sheath having a retractable tine fixation deployment means secured at a securing point on the flexible elongate tubular member of the inner catheter, wherein the securing point is located proximal to the distal section of the flexible elongate tubular member of the inner catheter, and wherein said retractable tine fixation deployment means includes a plurality of spaced apart expandable members, wherein the retractable tine fixation means has a non-deployed state and a distended deployed state, wherein the non-deployed state is used for advancing and removing the catheter and the distended deployed state is used for fixing the catheter to a targeted location of the body.

In an additional embodiment, the expanded spaced apart expandable members of the retractable tine fixation means at a distended deployed state have an outermost region, wherein the outermost region comprises needle-like penetrating means for securing the outermost region on a tissue. The needle-like penetrating means may comprise at least one grabbing needle-like object on each of the expandable members. The "needle-like penetrating means" in this invention is generally referred to having a sharp-end object for penetrating into a tissue, such as a needle, a screw, a wire, a tapered wire, and the like. The sharp-end object is preferably hidden within the catheter sheath during a retracted state and appears during a deployed state of the retractable fixation deployment means.

Another object of the invention is to provide a catheter with retractable fixation deployment means in which the fixation means can be deployed and undeployed between the mapping and/or ablation operations. Another object of the invention is to provide a catheter with retractable fixation deployment means in which the fixation means can be readily maneuvered, applied, and controlled by a deployment mechanism at the handle.

The catheter system further comprises a steering mechanism at the handle for controlling the deflection of said distal section of the flexible elongate tubular member of the inner catheter. Usually a rotating ring or a push-pull plunger is employed in the steering mechanism. In another embodiment, the steerable ablation catheter comprises a bi-directional deflection or multiple curves deflection of the tip section having retractable fixation deployment means. One end of the steering wire is attached at certain point of the distal section of the flexible elongate tubular member of said inner catheter. The other end is attached to the steering mechanism at the handle. The steering mechanism on a steerable catheter or device is well known to those who are skilled in the art.

At least one conducting wire which is secured to an electrode, passes through the lumen of the inner catheter and the interior void of the handle and is thereafter secured to a contact pin of the connector which is located at the proximal end of the handle. Therefrom, the conducting wire is connected to an external RF generator for ablation operations and/or to an EKG monitor for recording and display of the endocardial electrical signal.

In an additional embodiment, the catheter system further comprises a temperature sensing and a closed-loop temperature control mechanism for the catheter system having at least one temperature sensor on the distal section of the inner catheter. The location of the temperature sensor is preferably in the very proximity of one of the electrodes. In a still further embodiment, a method for operating an ablation catheter system of this invention further comprises a programmed temperature control mechanism for independently controlling the delivery of RF energy of each electrode of the ablation catheter.

In a still further embodiment, the distal section of the flexible elongate tubular member of the inner catheter comprises at least one electrode which is formed of a conducting material, wherein the material for the electrode may consist of conductive metals such as platinum, iridium, gold, silver, stainless steel, Nitinol, or an alloy of their mixture. The conducting metal and its fabrication to form an electrode to be used in a catheter is well known to those who are skilled in the art.

The catheter system of this invention further comprises a plurality in excess of three spaced apart expandable members for the retractable fixation deployment means. In a preferred embodiment, the catheter system comprises a plurality in excess of five spaced apart expandable members for the retractable fixation deployment means. The construction material for the expandable members may be selected from the group of polyethylene, polyurethane, polyether block amide polymer, stainless steel, high strength Nitinol and the like. The expandable members are part of the catheter sheath that has a continuous linear smooth surface when the retractable fixation deployment means is at its undeployed state. The expandable members have a pre-shaped memory and extend to their preformed shape when the retractable fixation deployment means is deployed.

In another embodiment, the catheter system of this invention further comprises expandable members of said retractable fixation deployment means having a preshaped memory, and extending at an angle of less than 90 degrees, preferably less than 45 degrees, relative to the distal portion of the longitudinal axis of the inner catheter when the deployment means is deployed. In a further embodiment, the catheter system further comprises expandable members of said retractable fixation deployment means having a preshaped memory, and extending with a curved concave or convex fashion at an acute angle relative to the distal portion of the longitudinal axis of the inner catheter when the deployment means is deployed.

In an alternate embodiment, a catheter system comprises: an inner catheter, having a flexible elongate tubular member having a distal section, and proximal and distal extremities, wherein the distal section has a thread for coupling purpose on the outside of the flexible elongate tubular member; an exchangeable handle attached to the proximal extremity of the inner catheter; at least one electrode is disposed at the distal section of the flexible elongate tubular member of said inner catheter; and a slidable catheter sheath, having a distal section, a proximal end, a distal end, and a lumen extending therebetween, wherein a matching tap hole for coupling purpose is disposed close to the distal end of the catheter sheath, and further having a retractable fixation deployment means at the distal section of the catheter sheath, wherein said retractable fixation deployment means including a plurality of spaced apart expandable members.

The catheter system further comprises a non-deployed state for said retractable fixation deployment means when said catheter sheath is advanced into the body of a patient and/or being removed from the body, and further comprising a distended deployed state for said retractable fixation deployment means when said catheter system is positioned at the target location of the body.

A method for operating a catheter system comprises: introducing the catheter system having an inner catheter and an outer catheter sheath under a non-deployed state into the body through a small surgery hole or through the natural body openings, and once approaching the target tissue, deploying the retractable fixation deployment means at distal section of said catheter sheath by a deployment mechanism located at the handle. The method for operating a catheter system of this invention further comprises at least one electrode mounted on the distal section of the flexible elongate tubular member of the inner catheter; and the expanded spaced apart expandable members of the retractable tine fixation means at the distended deployed state having an outermost region, wherein the outermost region comprises needle-like penetrating means for securing the outermost region on a tissue. The method for operating a catheter system further comprises measuring the endocardial electricity from or applying RF energy to the at least one electrode on the distal section of the flexible elongate tubular member of the inner catheter.

In another preferred embodiment, a method for operating a catheter system within a left atrium of a patient comprises the catheter system comprising a catheter sheath having a retractable tine fixation deployment means, wherein said retractable tine fixation deployment means includes a plurality of spaced apart expandable members, the expanded spaced apart expandable members having an outermost region, wherein the outermost region comprises needle-like penetrating means for securing the outermost region on a tissue. The method comprising the steps of: (a) introducing the catheter system into a pulmonary vein from the left atrium; (b) deploying the retractable tine fixation deployment means to expand the spaced apart expandable members; (c) advancing the catheter system until the expandable members contact the tissue; and (d) securing the catheter system in place by further advancing the needle-like penetrating means into the tissue.

The method for operating the catheter system further comprises the steps of after deploying the retractable fixation deployment means, measuring an endocardial electricity using the EKG monitor or applying RF current using the RF generating means, wherein the catheter system further comprising an EKG monitor, a RF generating means for generating RF current, and an electrical conductor connected to the RF generating means. The catheter system may further comprises at least one ultrasonic visible marker disposed on a distal section of the catheter sheath, adapted for advancing the catheter sheath into position by using the ultrasonically visible marker. The catheter system may further comprise a steering mechanism for controlling deflection of a distal section of the catheter system.

Another object of the invention is to provide a catheter and methods in which it is possible to view the area to be ablated prior to ablation to ensure that ablation is being carried out in an appropriate location. The distal section of the flexible elongate member of the inner catheter having retractable fixation deployment means is encoded with plurality of markers that are visible to ultrasonic energy. The markers have been provided in the form of encapsulated air bubbles.

The catheter system of the present invention has several significant advantages over known catheter or ablation techniques. In particular, the catheter system having a retractable fixation deployment means comprising needle-like objects for penetrating into a tissue may result in a firm and intimate tissue contact between the electrode and the target tissue during tissue ablation, resulting in a deep and large lesion which is highly desirable in tachycardia treatment.

BRIEF DESCRIPTION OF THE DRAWINGS

Additional objects and features of the present invention will become more apparent and the invention itself will be best understood from the following Detailed Description of the Preferred Embodiments, when read with reference to the accompanying drawings.

DETAILED DESCRIPTION OF THE PREFERRED EMBODIMENTS

Figure 1:
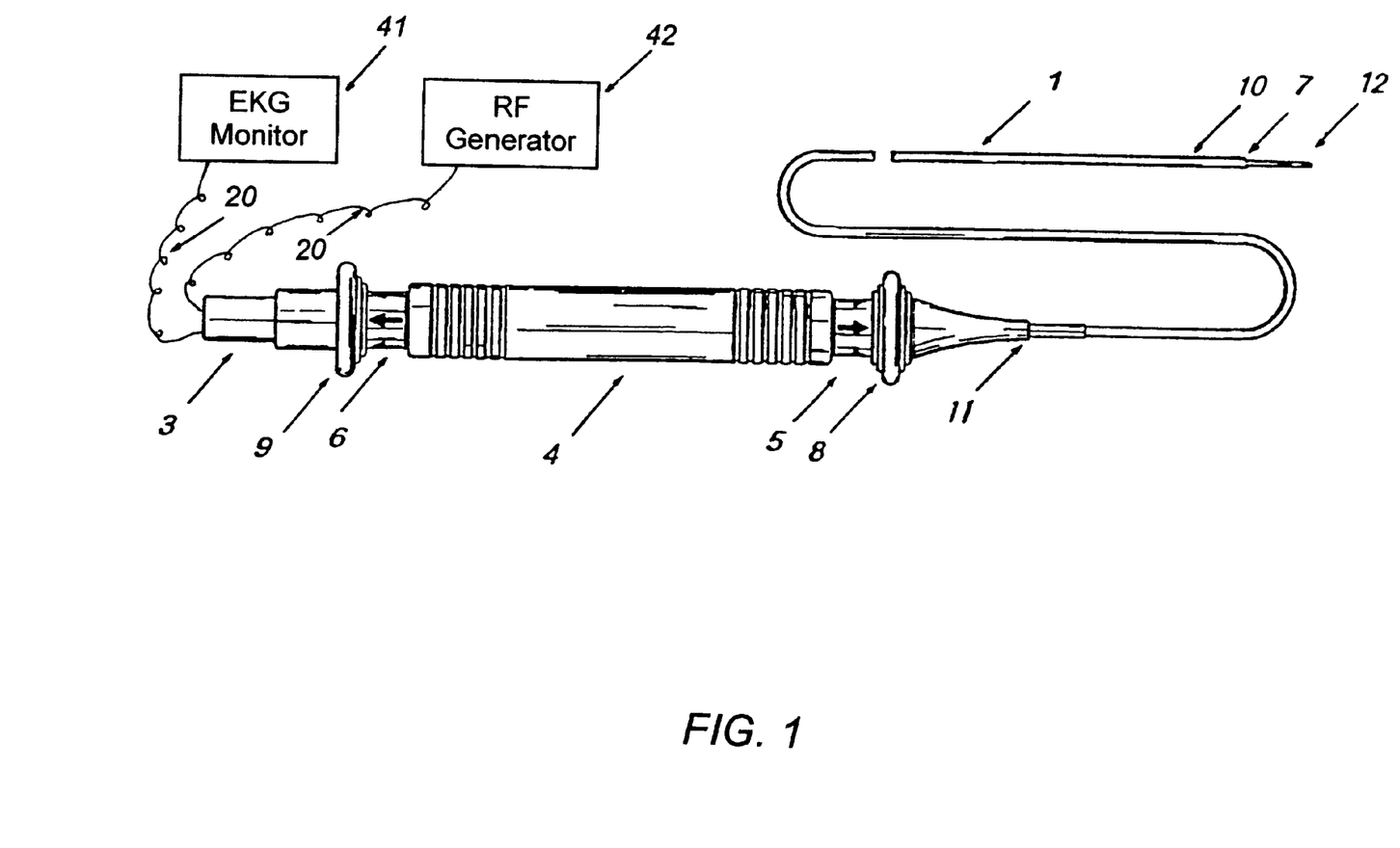
FIG. 1 is an overall view of the catheter system having a retractable fixation deployment means constructed in accordance with the principles of the present invention.

FIG. 1 shows an overall view of the catheter system having a distal section comprising retractable fixation deployment means, wherein the retractable fixation deployment means has needle-like penetrating means. A catheter system constructed in accordance with the principles of the present invention comprises a catheter sheath 1 having a distal tip section 10, a distal end 7, a proximal end 11, and at least one lumen 61 extending between the distal end 7 and the proximal end 11. The catheter also comprises an inner catheter 12 that is longer than the catheter sheath 1 and is located within the lumen of the catheter sheath 1. A handle 4 is attached to the proximal end 11 of said catheter sheath 1.

The connector 3 secured at the proximal end of the catheter system, is part of the handle 4. The handle has one steering mechanism 5. The steering mechanism 5 is to deflect the tip section 13 of the inner catheter 12 for catheter maneuvering and positioning. By pushing the front plunger 8 of the handle 4, the tip section of the flexible elongate member of the inner catheter 12 deflects to one direction. By pulling the front plunger 8, said tip section returns to its neutral position. In another embodiment, the steering mechanism 5 at the handle 4 comprises means for providing a plurality of deflectable curves on the distal tip section 13 of the inner catheter.

Figure 2:
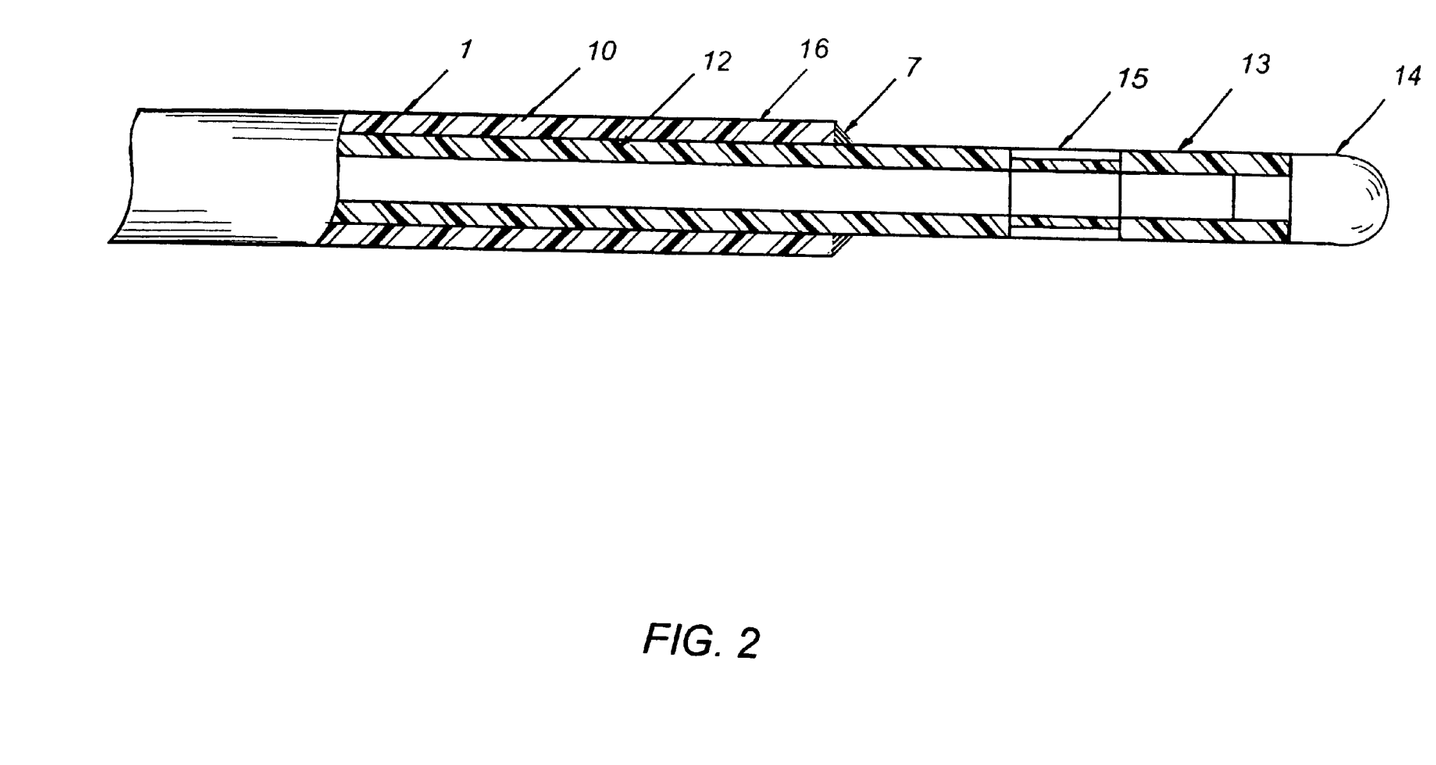
FIG. 2 is a close-up view of the distal section of the catheter system at a non-deployed state.

FIG. 2 shows a close-up view of the distal section of the catheter system having retractable fixation deployment means at a non-deployed state. In one embodiment, the distal section 13 of the inner catheter 12 has a tip electrode 14 and at least one band electrode 15. The electrode is constructed of a conducting material. The distal section of the catheter system having retractable fixation deployment means 16 at a non-deployed state, wherein the retractable fixation deployment means 16 is secured at a securing point 7 on the flexible elongate tubular member of the inner catheter 12.

Figure 3:
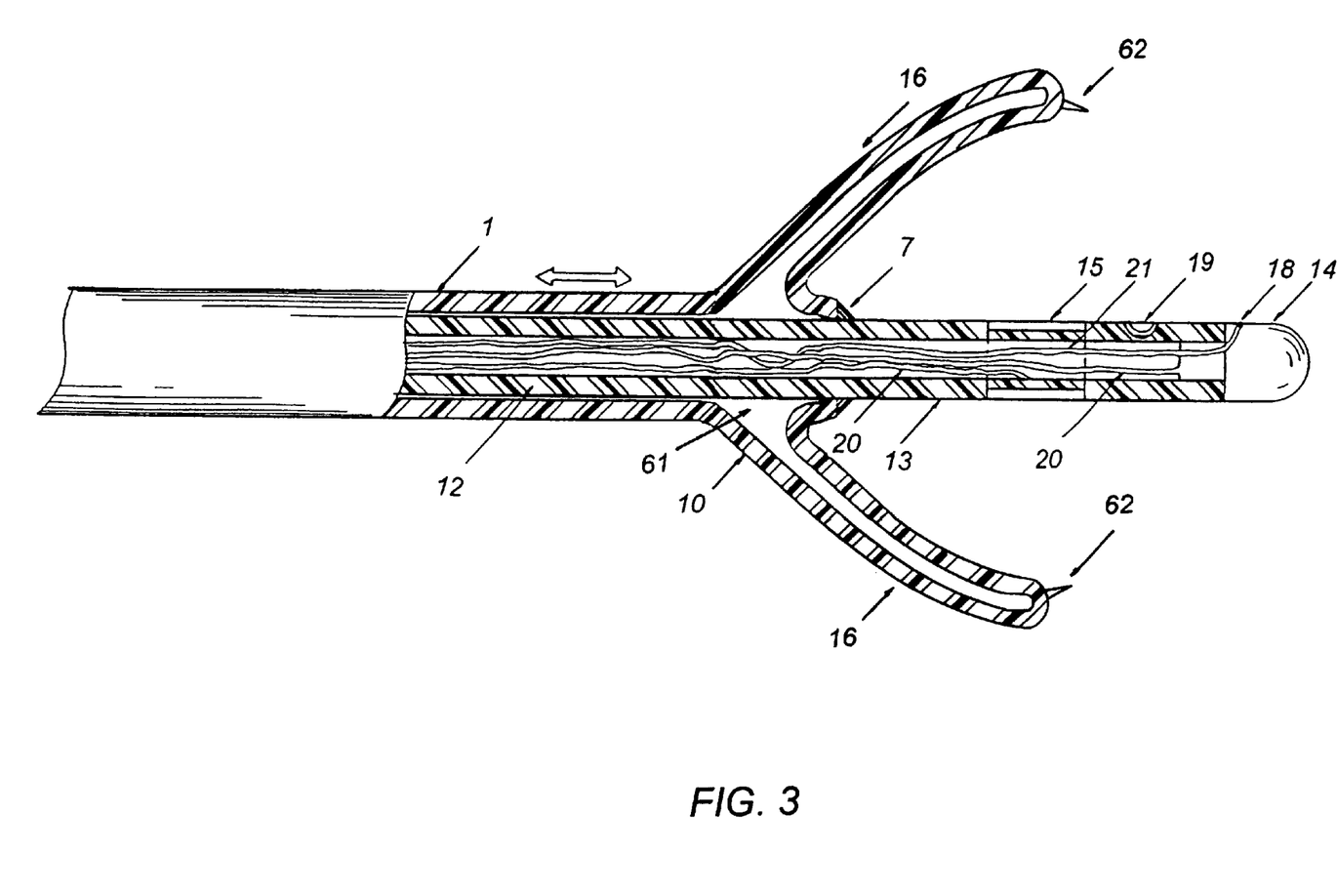
FIG. 3 is a close-up view of the distal section of the catheter system, having needle-like penetrating means, at a fully deployed state.

FIG. 3 shows a close-up view of the distal section of the catheter system having retractable fixation deployment means 16 and a needle-line penetrating means 62 at a deployed state. The distal section 10 of the catheter sheath 1 has a retractable fixation deployment means 16 at a securing point 7 on the flexible elongate tubular member of the inner catheter 12, wherein the securing point 7 is located proximal to the distal section 13 of the flexible elongate tubular member of the inner catheter 12. The deployment of the retractable fixation deployment means 16 is controlled by a deployment mechanism 6 at the handle 4 (FIG. 1). In one preferred embodiment, a controlling ring 9 is used to deploy the retractable fixation deployment means 16 at the distal section 10 of the catheter sheath 1.

Figure 6:
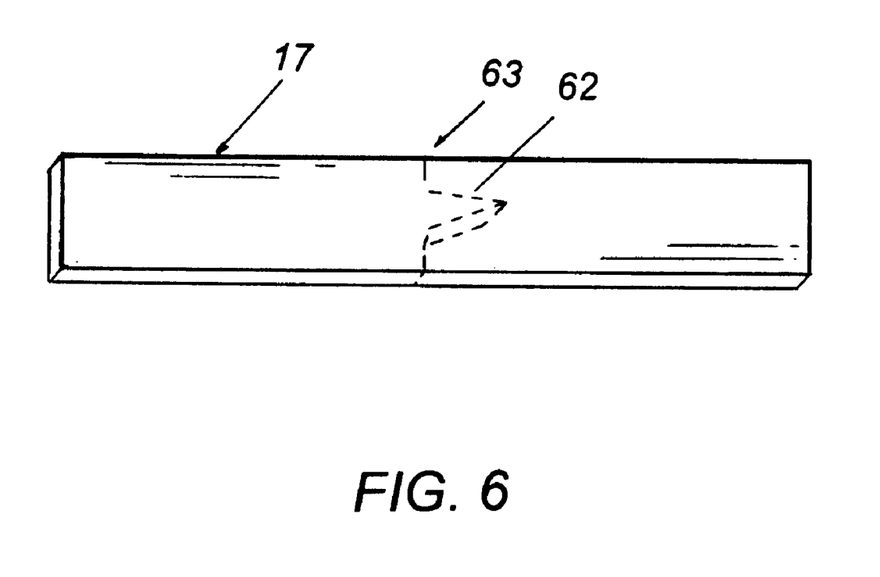
FIG. 6 is a close-up view of one expandable member of the retractable fixation deployment means at a non-deployed state.
Figure 7:
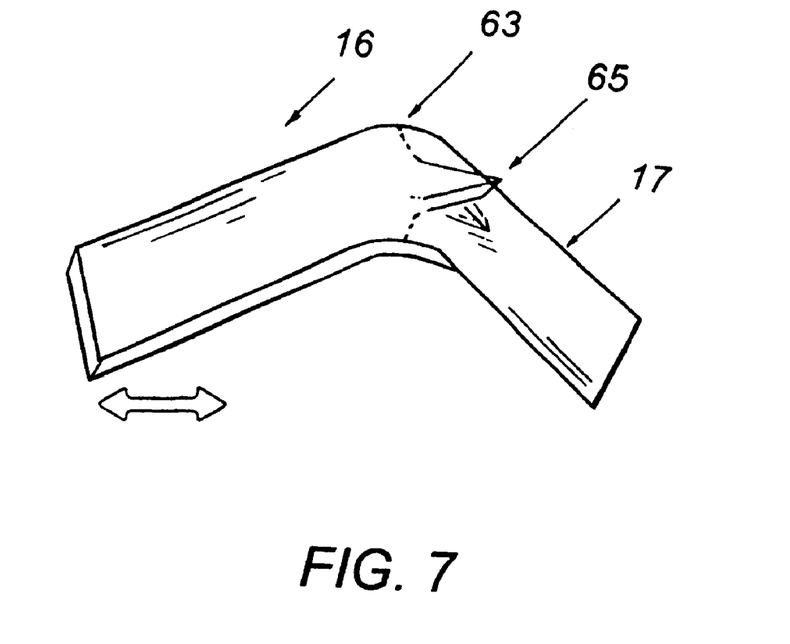
FIG. 7 is a close-up view of one expandable member of the retractable fixation deployment means at a partially deployed state.

The needle-like penetrating means 62 is located adjacent to the folding line 63 of an expandable member. FIG. 6 shows a close-up view of one expandable member 17 of the retractable fixation deployment means 16 at a non-deployed state. The needle-like penetrating means 62 comprises at least one grabbing needle-like object 65 on each of the expandable members 17, wherein the needle-like object 65 has a sharp-end for penetrating into a tissue. The needle-like object 65 is selected from a group consisting of a needle, a screw, a wire, a tapered wire, and the like. FIG. 7 shows a close-up view of one expandable member 17 of the retractable fixation deployment means 16 at a partially deployed state. The sharp-end object 65 is preferably hidden within the expandable member 17 of the catheter sheath 1 during a retracted state and appears during a deployed state of the retractable fixation deployment means 16.

Figure 4:
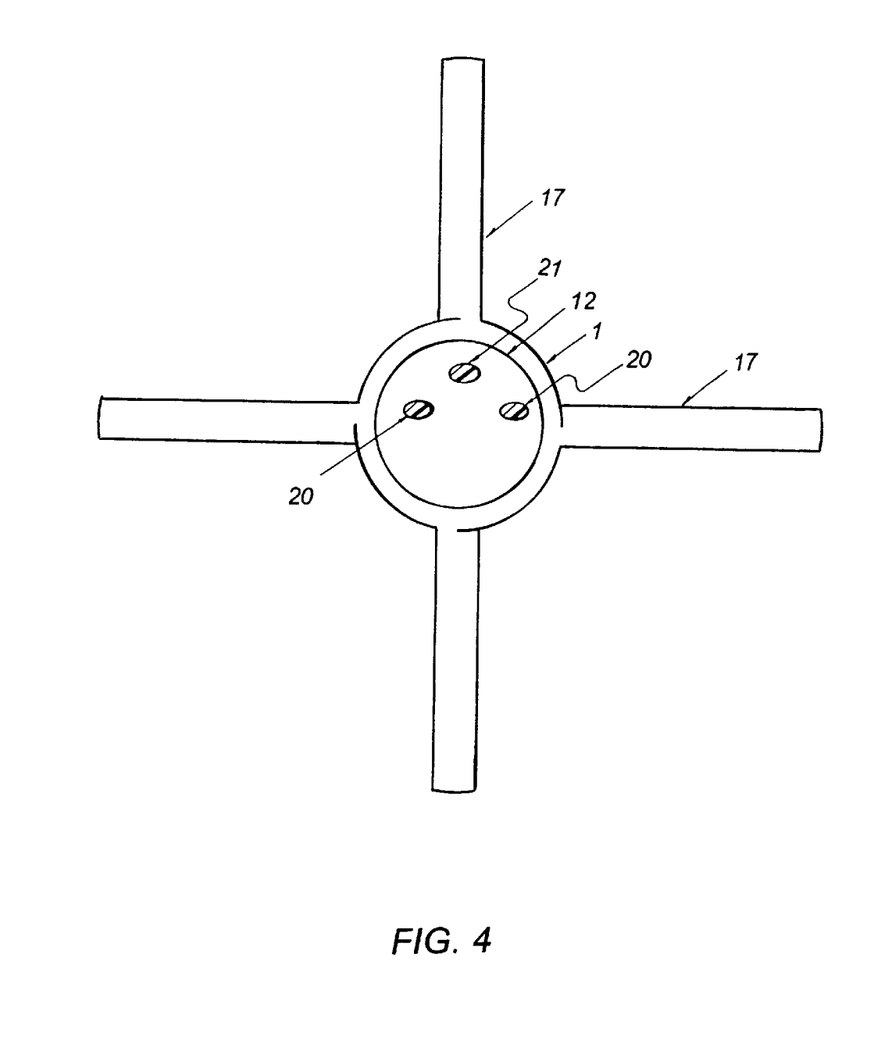
FIG. 4 is a cross-sectional view of the expandable members of the catheter sheath of FIG. 3.

FIG. 4 shows a cross-sectional view of the catheter system that comprises expandable members 17 of the retractable fixation deployment means 16, having a preshaped memory. In one further embodiment, the expandable members extend with a curved concave or convex fashion at an acute angle relative to the proximal side of the longitudinal axis of the inner catheter 12 when the deployment means 16 is deployed. The catheter system has at least one temperature sensor 18 and ultrasonic imaging capabilities. In order to enhance the ablation positioning of said ablation catheter, the electrode is encoded with at least one marker 19 which is visible to ultrasonic energy. Such markers 19 are provided in the form of encapsulated air bubbles. Several markers 19 are placed in the proximity of the electrodes 14 or 15 in a way so that the exact location of the distal section 13 is visible to an external ultrasonic energy. By way of example, the bubble in a marker can be formed by introducing air by a syringe penetrating the wall of the substrate sheath of said catheter sheath and thereafter is sealed by epoxy.

The electrode has an insulated conducting wire 20 secured to an electrode, which passes through the lumen of the inner catheter 12 and is soldered to a contact pin of the connector 3 at the proximal end of the handle 4. The conducting wire from the connector end is externally connected to an EKG 41 for diagnosis or to a RF generator 42 during an electrophysiology ablation procedure. Therefrom, the RF energy is transmitted through the conducting wire to the electrode and delivered the energy to the target tissue.

A temperature sensor 18, either a thermocouple means or a thermister means, is constructed at the proximity of the at least one electrode 14 or 15 to measure the tissue contact temperature when RF energy is delivered. The temperature sensing wire 21 from the thermocouple or thermister is connected to one of the contact pins of the connector 3 on the handle 4 and externally connected to a temperature transducer and to a closed-loop temperature controller. The temperature reading is thereafter relayed to a closed-loop control mechanism to adjust the RF energy output. The RF energy delivered is thus controlled by the temperature sensor reading or by a pre-programmed control algorithm.

Figure 5:
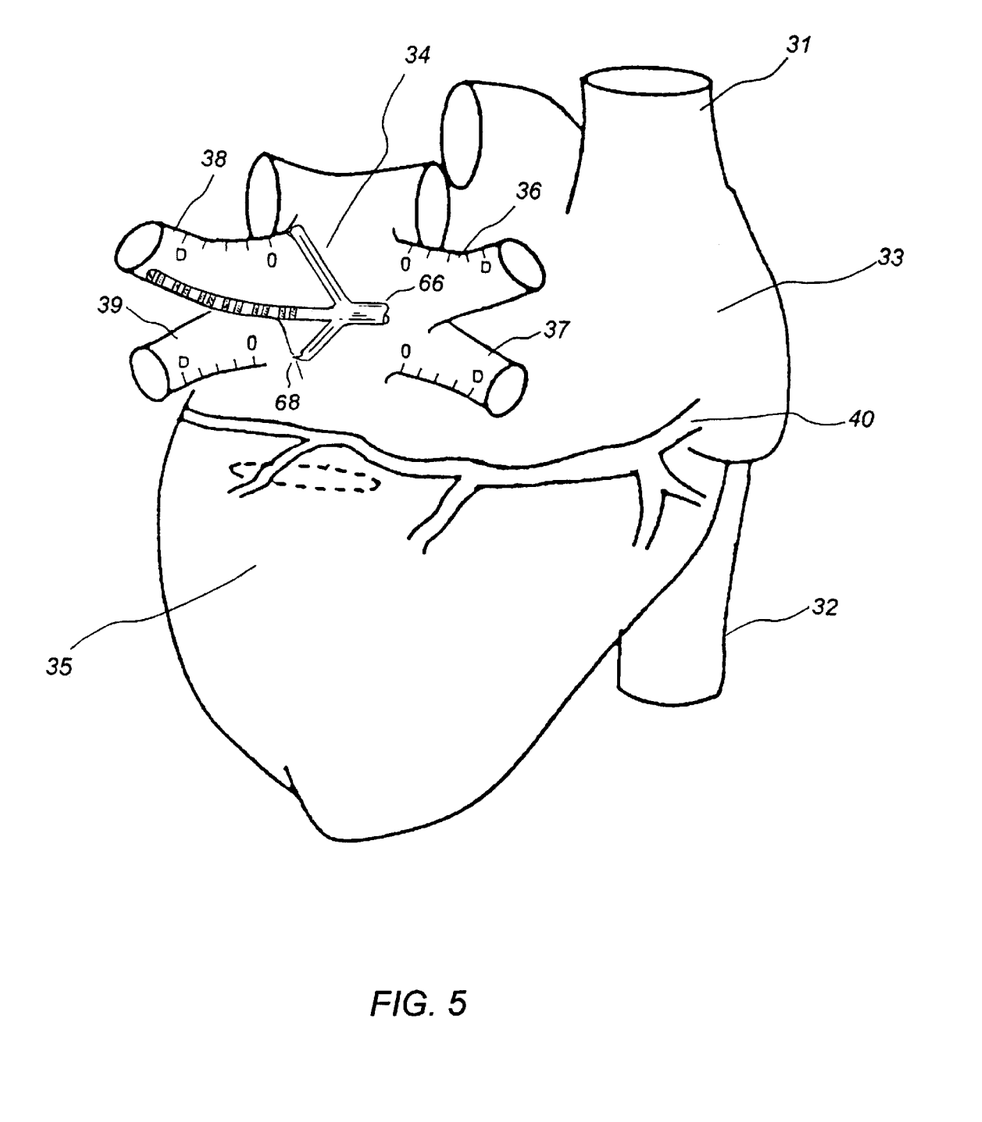
FIG. 5 is a perspective view of the catheter system securing into a tissue using the needlelike penetrating means of the present invention.

FIG. 5 shows a perspective view of the catheter system simulating an operation inside a heart that securing the catheter into a tissue using the needle-like penetrating means 62 of the present invention. To better illustrate the application of the present invention, a human heart is shown in FIG. 5. Blood returned from superior vena cava 31 and inferior vena cava 32 flows back to the right atrium 33. A coronary sinus 40 is part of the coronary artery system to provide nutrient to the heart tissue, wherein the heart also comprises a left atrium 34, a left ventricle 35 and a right ventricle. A catheter 66 of the present invention is inserted into the left atrium 34 using a standard vascular inserting procedure, such as a trans-septal procedure A normal people has four pulmonary veins: right superior pulmonary vein 36, right inferior pulmonary vein 37, left superior pulmonary vein 38, and left inferior pulmonary vein 39. In one example, a catheter 66 is inserted into the left superior pulmonary vein 38. After the distal portion of the catheter 66 is inside the vein 38, the retractable fixation deployment means 16 is deployed. Each of the expandable members 17 is expanded and the needle-like object 65 on each expanded member 17 is deployed and points to the distal direction of the catheter 66 to penetrate into the heart tissue 68 for fixation purposes. After an electrophysiology procedure is finished, the needle-like object 65 is dislodged off the tissue and the expanded members 17 are retracted to their non-deployed manners for withdrawal the catheter 66 from the body of a patient.

Figure 8:
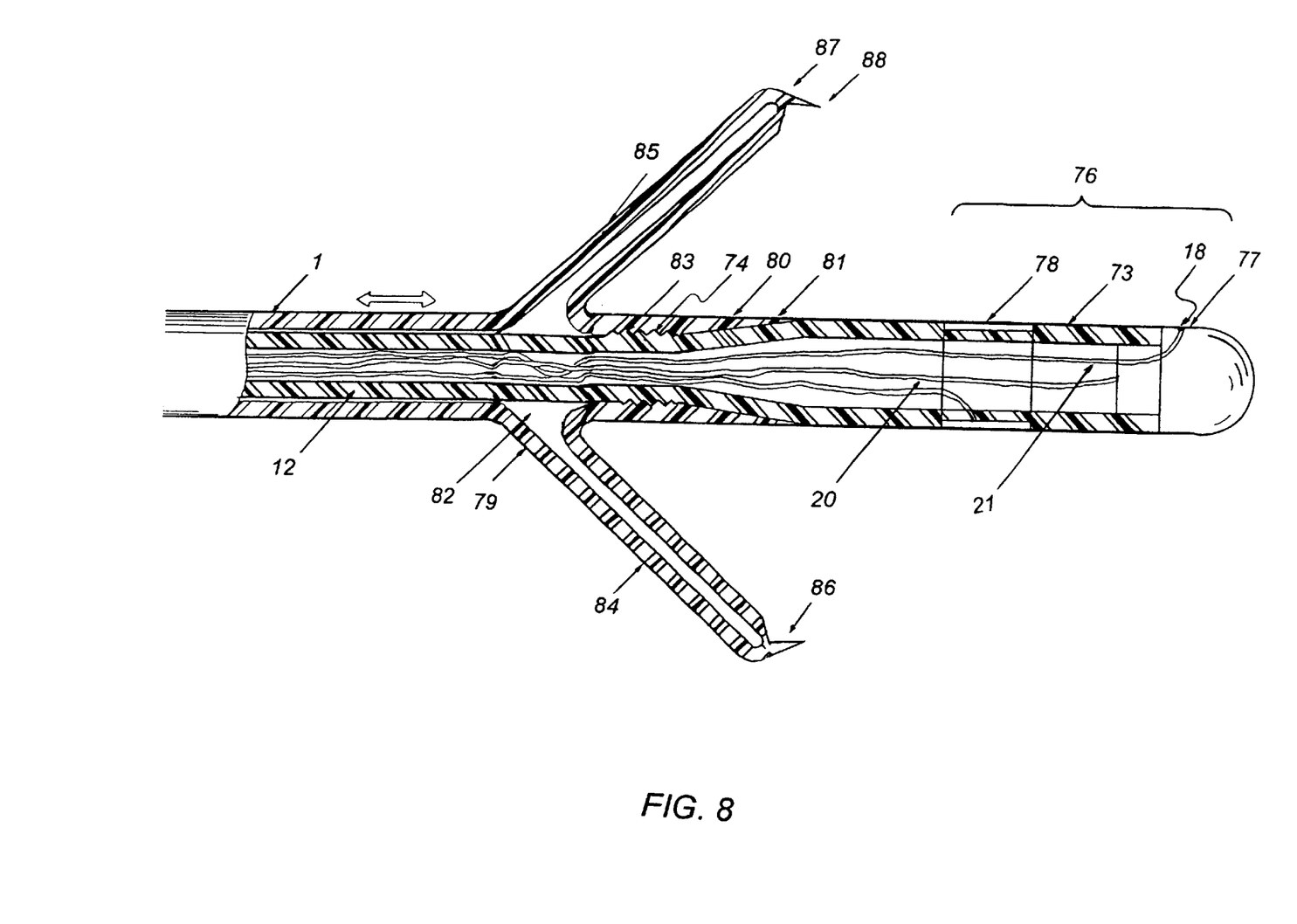
FIG. 8 is a close-up view of the distal section of an alternate preferred catheter system, having needle-like penetrating means, at a fully deployed state.

FIG. 8 shows a close-up view of the distal section of an alternate preferred catheter system at a non-deployed state. The catheter system comprises an inner catheter 73, having a flexible elongate tubular member 75 having a distal section 76, and proximal and distal extremities, wherein the distal section has a thread 74 on the outside of the flexible elongate tubular member 75; an exchangeable handle attached to the proximal extremity of the inner catheter; at least one electrode 77 or 78 is disposed at the distal section 76 of the flexible elongate tubular member 75 of said inner catheter 73; and a slidable catheter sheath 79, having a distal section 80, a proximal end, a distal end 81, and a lumen 82 extending therebetween, wherein a matching tap hole 83 is disposed close to the distal end of the catheter sheath 79, and further having a retractable fixation deployment means 84 at the distal section of the catheter sheath 79, wherein said retractable fixation deployment means includes a plurality of spaced apart expandable members 85. During operation, the inner catheter is inserted into the body of a patient, the inner catheter alone may function as an electrophysiology catheter for the purpose of mapping and/or ablation. When the catheter fixation need arises, the exchangeable handle is removed from the inner catheter, and a catheter sheath of this invention is inserted over the inner catheter. The catheter sheath and the inner catheter are engaged by coupling the tap hole of the catheter sheath and the thread of the inner catheter. After replacing the exchangeable handle, the catheter system is ready for operation having retractable fixation deployment means. After the operation is concluded, the coupled catheter system, including the catheter sheath and the inner catheter, is deployed first and is thereafter removed from the body of a patient together as a catheter system.

A needle-like penetrating means 86 is located adjacent to the folding line 87 of an expandable member 85. The needle-like penetrating means 86 comprises at least one grabbing needle-like object 88 on each of the expandable members 85, wherein the needle-like object 88 has a sharp-end for penetrating into a tissue. The needle-like object 88 is selected from a group consisting of a needle, a screw, a wire, a tapered wire, and the like. The sharp-end object 88 is preferably hidden within the expandable member 85 of the catheter sheath 79 during a retracted state and appears during a deployed state of the retractable fixation deployment means 84.

From the foregoing, it should now be appreciated that an improved ablation catheter having retractable fixation deployment means and needle-like penetrating means has been disclosed for mapping and/or ablation procedures, including endocardial, epicardial, or body tissue. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:
   (a) a catheter sheath having a distal section, a distal end, a proximal end, and at least one lumen extending between the distal end and the proximal end;
   (b) a handle attached to the proximal end of said catheter sheath;
   (c) an inner catheter, which is longer than said catheter sheath and is located inside the lumen of the catheter sheath comprising a flexible elongate tubular member having a distal section, a proximal extremity and a distal extremity, at least one electrode mounted on the distal section of the flexible elongate tubular member of the inner catheter, and wherein said handle is attached to the proximal extremity of the inner catheter;
   (d) the distal section of said catheter sheath having a means for retractable electrode-tine fixation deployment secured at a securing point on the flexible elongate tubular member of the inner catheter, wherein the securing point is located proximal to the distal section of the flexible elongate tubular member of the inner catheter, and wherein said means for retractable electrode-tine fixation deployment includes a plurality of spaced apart expandable members, wherein a means for retractable electrode-tine fixation has a non-deployed state and a distended deployed state, wherein the non-deployed state is adapted for advancing and removing the catheter and the distended deployed state is adapted for fixing the catheter to a targeted location; and
   (e) the expanded spaced apart expandable members of the means for retractable electrode-tine fixation at a distended deployed state having an outermost region, wherein the outermost region comprises needle penetrating means for securing the outermost region on a tissue firmly at the distended deployed state wherein the needle penetrating means in the deployed state points to the distal section of the inner catheter.

2. The catheter system of claim 1, wherein the plurality of spaced apart expandable members has at least 4 spaced apart members.

3. The catheter system as in claim 1 further comprising at least one ultrasonic visible marker disposed on the distal section of the flexible elongate tubular member of the inner catheter.

4. The catheter system as in claim 1 further comprising a steering mechanism at the handle for controlling the deflection of the distal section of the flexible elongate tubular member of said inner catheter.

5. The catheter system of claim 1, wherein the expandable members of said means for retractable electrode-tine fixation deployment have a preshaped memory, and extend at an angle of less than 90 degrees relative to the distal section of the elongate tubular member of the inner catheter when the deployment means is deployed.

6. The catheter system of claim 1, wherein the expandable members of said means for retractable electrode-tine fixation deployment have a preshaped memory, and extend at an angle of less than 45 degrees relative to the distal section of the elongate tubular member of the inner catheter when the deployment means is deployed.

7. The catheter system of claim 1, wherein the expandable members of said retractable fixation deployment means have a preshaped memory, and extend with a curved fashion at an acute angle relative to the distal section of the elongate tubular member of the inner catheter when the deployment means is deployed.

8. The catheter system as in claim 1 further comprising a temperature sensor mounted next to the at least one electrode at the distal section of the flexible elongate tubular member of the inner catheter and providing sensing signals for a closed-loop temperature controller for the catheter system.

9. A method for operating a catheter system within a body of a patient comprising the steps of:
   (a) introducing the catheter system having an inner catheter and an outer catheter sheath under a non-deployed state into the body through a small surgery hole or through a natural body opening, wherein the catheter system comprises a catheter sheath with a distal section, a distal end, a proximal end, and at least one lumen extending therebetween; a handle attached to the proximal end of the catheter sheath; an inner catheter, which is longer than said catheter sheath and is located inside the lumen of the catheter sheath, comprising a flexible elongate tubular member having a distal section, a proximal extremity and a distal extremity, at least one electrode mounted on the distal section of the flexible elongate tubular member of the inner catheter, and wherein said handle is attached to the proximal extremity of the inner catheter; the distal section of said catheter sheath having a means for retractable electrode-tine fixation deployment secured at a securing point on the flexible elongate tubular member of the inner catheter, wherein the securing point is located proximal to the distal section of the flexible elongate tubular member of the inner catheter, and wherein said means for retractable electrode-tine fixation deployment includes a plurality of spaced apart expandable members, wherein a means for retractable electrode-tine fixation has a non-deployed state and a distended deployed state, wherein the non-deployed state is adapted for advancing and removing the catheter and the distended deployed state is adapted for fixing the catheter to a targeted location; and the expanded spaced apart expandable members of the means for retractable electrode-tine fixation at the distended deployed state having an outermost region, wherein the outermost region comprises needle penetrating means for securing the outermost region on a tissue firmly at the distended deployed state wherein the needle penetrating means in the deployed state points to the distal section of the inner catheter; and (b) once approaching the target tissue, deploying the means for retractable electrode-tine fixation deployment at the distal section of said catheter sheath by a deployment mechanism for deploying retractable electrode-tine fixation that is located at the handle.

10. The method for operating the catheter system as in claim 9, the catheter system comprising an EKG monitor, a RF generating means, and an electrical conductor connected to the at least one electrode, the method further comprising the steps of: after deploying the means for retractable electrode-tine fixation deployment, measuring the endocardial electricity from the electrical conductor using the EKG monitor or applying RF energy through the electrical conductor to the at least one electrode on the distal section of the flexible elongate tubular member of the inner catheter.

11. The method for operating the catheter system as in claim 9, the catheter system comprising at least one ultrasonic visible marker disposed on the distal section of the flexible elongate tubular member of the inner catheter, the method further comprising advancing the at least one electrode into position by using the ultrasonically visible marker.

12. The method for operating the catheter system as in claim 9, the catheter system further comprising a steering mechanism at the handle for controlling the deflection of the distal section of the flexible elongate tubular member of said inner catheter.

* * * * *